US010582904B2

(12) United States Patent
Pizaine et al.

(10) Patent No.: US 10,582,904 B2
(45) Date of Patent: Mar. 10, 2020

(54) DETERMINING C-ARM ANGULATION FOR VALVE POSITIONING

(71) Applicant: KONINKLIJKE PHILIPS N.V., Eindhoven (NL)

(72) Inventors: Guillaume Julien Joseph Pizaine, Issy-les-Moulineaux (FR); Olivier Pierre Nempont, Suresnes (FR); Pieter Gerben Eshuis, Best (NL); Javier Olivan Bescos, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 151 days.

(21) Appl. No.: 15/580,567

(22) PCT Filed: Jun. 15, 2016

(86) PCT No.: PCT/EP2016/063794
§ 371 (c)(1),
(2) Date: Dec. 7, 2017

(87) PCT Pub. No.: WO2016/202881
PCT Pub. Date: Dec. 22, 2016

(65) Prior Publication Data
US 2018/0153489 A1 Jun. 7, 2018

(30) Foreign Application Priority Data
Jun. 17, 2015 (EP) .................................... 15305940

(51) Int. Cl.
*H05G 1/02* (2006.01)
*A61B 6/00* (2006.01)
(Continued)

(52) U.S. Cl.
CPC ............ *A61B 6/4441* (2013.01); *A61B 6/481* (2013.01); *A61B 6/487* (2013.01); *A61B 6/503* (2013.01);
(Continued)

(58) Field of Classification Search
CPC ....... A61B 6/504; A61B 6/5211; A61B 6/545; A61B 6/5223; A61B 6/4441; A61B 6/481; A61B 34/10
See application file for complete search history.

(56) References Cited

U.S. PATENT DOCUMENTS

2009/0306500 A1 12/2009 Rahn
2010/0014629 A1* 1/2010 Boese .................. A61B 6/4441
378/8
(Continued)

FOREIGN PATENT DOCUMENTS

WO 2015074869 A1 5/2015

OTHER PUBLICATIONS

Samim et al., "Automated 3D analysis of pre-procedural MDCT to predict annulus plane angulation and C-Arm positioning," 2013, JACC: Cardiovascular Imaging, vol. 6, No. 2, pp. 238-248. (Year: 2013).*
(Continued)

*Primary Examiner* — Kiho Kim

(57) ABSTRACT

The present invention relates to determining optimal C-arm angulation for heart valve positioning. In order to further improve the workflow in relation with the correct positioning of a valve prosthesis, it is described to provide (12) a 2D image of an aortic root of a heart of a patient, wherein the 2D image comprises three cusps of the heart in a visible and distinct manner. Further, 2D positions of the three cusps are indicated (14) in the 2D image. An analytical 3D model of the aortic cusp locations is provided (16), and the 3D positions of the three cusps are computed (18) based on the 2D positions and the analytical 3D model. Still further, an optimal C-arm angulation is computed (20) based on the computed 3D positions of the cusps, wherein, in the optimal C-arm angulation, the three cusps are aligned in a 2D image.
(Continued)

The optimal C-arm angulation is then provided for further image acquisition steps.

18 Claims, 5 Drawing Sheets

(51) Int. Cl.
*A61B 34/10* (2016.01)
*A61F 2/24* (2006.01)

(52) U.S. Cl.
CPC ............ *A61B 6/504* (2013.01); *A61B 6/5211* (2013.01); *A61B 6/545* (2013.01); *A61B 34/10* (2016.02); *A61B 6/5223* (2013.01); *A61F 2/24* (2013.01)

(56) References Cited

U.S. PATENT DOCUMENTS

| | | | |
|---|---|---|---|
| 2011/0052026 A1* | 3/2011 | Liao | G06T 7/73 382/131 |
| 2011/0096969 A1* | 4/2011 | Zheng | G06K 9/00214 382/131 |
| 2012/0163686 A1* | 6/2012 | Liao | G06T 7/33 382/130 |
| 2012/0250964 A1* | 10/2012 | Pfister | A61B 6/12 382/130 |
| 2012/0293498 A1 | 11/2012 | Schormans | |
| 2012/0323545 A1* | 12/2012 | Aulbach | A61B 6/504 703/11 |
| 2013/0129173 A1* | 5/2013 | Grbic | G06T 7/0012 382/131 |
| 2013/0266123 A1* | 10/2013 | Yoshida | A61B 6/545 378/98.5 |
| 2013/0266126 A1 | 10/2013 | Dunne | |
| 2015/0223773 A1* | 8/2015 | John | A61B 8/0841 600/424 |

OTHER PUBLICATIONS

Kasel, Albert M. et al "Standardized Imaging for Aortic Annular Sizing", JACC Cardiovascular Imaging, vol. 6, No. 2, 2013.

* cited by examiner

DETERMINING C-ARM ANGULATION FOR VALVE POSITIONING

CROSS-REFERENCE TO PRIOR APPLICATIONS

This application is the U.S. National Phase application under 35 U.S.C. § 371 of International Application No. PCT/EP2016/063794, filed on Jun. 15, 2016, which claims the benefit of European Patent Application No. 15305940.7, filed on Jun. 17, 2015. These applications are hereby incorporated by reference herein.

FIELD OF THE INVENTION

The present invention relates to an apparatus for determining a C-arm angulation for heart valve positioning, to a medical imaging system, and to a method for determining C-arm angulation for heart valve positioning, as well as to a computer program element and a computer readable medium.

BACKGROUND OF THE INVENTION

For example, during trans-aortic valve implantation (TAVI) procedures, the positioning of the valve prosthesis is an important task. The correct positioning, for example, may be beneficial in order to minimize paravalvular aortic leaks, which may affect future heart performance. The exact positioning of the valve may be determined during the planning stage by an interventionist to ensure that the coronary ostia will not be obstructed and to minimize the risk of paravalvular aortic leaks. In other words, the correct positioning is aimed to get the best possible outcome of the procedure. As an example, US 2011/0096969A1 relates to a method and system for shape constraint aortic valve landmark detection. The landmark detection is provided using 3D medical images. However, it has been shown that the determination requires 3D medical images and can thus be cumbersome. The detected landmarks may then be used for the positioning of a valve prosthesis.

SUMMARY OF THE INVENTION

There may thus be a need to further improve the workflow in relation with the correct positioning of a valve prosthesis.

The object of the present invention is solved by the subject-matter of the independent claims, wherein further embodiments are incorporated in the dependent claims. It should be noted that the following described aspects of the invention apply also for the apparatus for determining a C-arm angulation for heart valve positioning, the medical imaging system, the method for determining a C-arm angulation for heart valve positioning, and to the computer program element and the computer readable medium.

According to a first aspect of the present invention, an apparatus for determining a C-arm angulation for heart valve positioning is provided. The apparatus comprises an input device, a processing device, and an output device. The input device is configured to provide a 2D image of an aortic root of a heart of a patient. The 2D image comprises three cusps of the heart in a visible and distinct manner. The input device is further configured to provide an analytical 3D model of the aortic cusp locations. The processing device is configured to indicate 2D positions of the three cusps in the 2D image, and to compute 3D positions of the three cusps based on the 2D positions and the analytical 3D model. The processing device is further configured to calculate a C-arm angulation based on the computed 3D positions of the cusps. The calculated angulation is such that, in a further 2D image acquired using said angulation, the three cusps are aligned in a 2D image. The output device is configured to provide the C-arm angulation.

As a result, only a 2D image of the aortic root area of the heart of the patient is needed, and by transferring the information concerning the positions of the three cusps in the 2D image into the 3D model world, the respective spatial information is provided that is then used for determining a C-arm angulation that is optimized for the heart valve positioning.

Within the context of the present patent application, the angulation thus determined or calculated is also referred to as an 'optimal' C-arm angulation. With, for example, a C-arm of an X-ray imaging device positioned in accordance with the calculated angulation, projection images may be acquired as the further 2D images which optimally depict the cusps of the aortic root. That is, the calculated C-arm angulation may provide an orientation for an X-ray imaging device that enables the acquisition of live X-ray images in which the three cusps of the aovisible to an interventionalist during, for example, heart valve replacement in an optimal manner.

According to a second aspect, a medical imaging system is provided that comprises an X-ray imaging device and an apparatus for determining a C-arm angulation for heart valve positioning according to the above-mentioned example. The imaging device is configured to provide the 2D image as a live 2D X-ray image. The apparatus is further configured to provide the computed C-arm angulation to the X-ray imaging device for acquisition of the further 2D image as a live 2D X-ray image. Preferably, a sequence of such further 2D images may be acquired.

As a result, the medical imaging system used for X-ray guidance during heart valve positioning, for example, provides also the 2D image as a live 2D X-ray image in order to then compute the optimal C-arm angulation, which can then be used for further image acquisition.

According to a third aspect, a method for determining a C-arm angulation for heart valve positioning is provided. The method comprises the following steps:

a) providing a 2D image of an aortic root of a heart of a patient, wherein the 2D image comprises three cusps of the heart in a visible and distinct manner;

b) indicating 2D positions of the three cusps in the 2D image;

c) providing an analytical 3D model of the aortic cusp locations;

d) computing 3D positions of the three cusps based on the 2D positions and the analytical 3D model; and e) computing a C-arm angulation based on the computed 3D positions of the cusps, wherein, in a further 2D image acquired using the C-arm angulation, the three cusps are aligned, and further providing the optimal C-arm angulation.

As a result, a facilitated way of supporting an interventionist during, for example, heart valve replacement, is provided by determining the optimal C-arm angulation based on a 2D image of the aortic root, in combination with an analytical 3D model. Hence, the image acquisition needed for providing the base for the computing of the optimal C-arm angulation is reduced to a minimum, which also means at least some relieve in view of the X-ray doses applied to a patient. Further, also the computational task is reduced to a minimum by using the data from the 2D image and combine this with information comprised in the analytical 3D model.

According to an example, each cusp comprises a hinge point, and, in the aligned state, the hinge points of the cusps are arranged on a common line.

As a result, a further facilitated way of image analysis is provided, since the hinge points can easily be identified in the 2D image, and the determination of the optimal viewing angle for the C-arm is related to a simplified model in form of the common line, on which the hinge points are arranged.

According to an example, the three cusps are equidistant with a standard distance in the order of the aortic radius.

Thus, a robust and further facilitated model or assumption is used that further improves the determination of the optimal viewing angle.

According to an example, the analytical 3D model comprises a spatial arrangement of the three cusps in a patient-related manner.

Thus, the 3D model is so-to-speak adapted to the patient under examination, for example based on previously acquired 3D image information. Hence, the transfer from the information of the 2D image into the 3D space of the analytical 3D model is further improved.

According to an example, the 2D image is a single live 2D X-ray image. The optimal C-arm angulation may then be provided for further acquisition of further live 2D X-ray images.

According to an example, the 2D image in the first step, i.e. step a), relates to a near-optimal C-arm angulation.

By starting from a so-to-speak pre-optimized preview, or initial 2D image acquisition, the overall result is improved and the processing steps are facilitated.

According to another example, it is further provided to rotate the C-arm to match the determined C-arm optimal angulation and to acquire 2D image data.

For example, the further acquired 2D image data can then be used for guidance or observations for the positioning procedure of positioning the valve prosthesis.

According to an example, the indicating of the 2D positions of the three cusps of the heart in the 2D image is provided automatically by an automatic detection.

Hence, the burden for the surgeon is further relieved.

In an example, the indication of the 2D positions is provided by manual user interaction.

According to an aspect, one first angiogram is acquired with a near optimal C-arm angulation, where at least the three cusps are clearly visible and distinct. In that angiogram, the three cusps are either indicated manually by the interventionist or automatically detected. From the 2D positions of the three cusps, an algorithm computes the 3D positions of the cusps. An analytical model of the aortic cusp locations is provided to ensure a unique 3D solution. From the 3D positions of the cusps, the optimal C-arm angulation can be derived. In an example, the C-arm is rotated to match this optimal angulation, for example via automatic position control.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
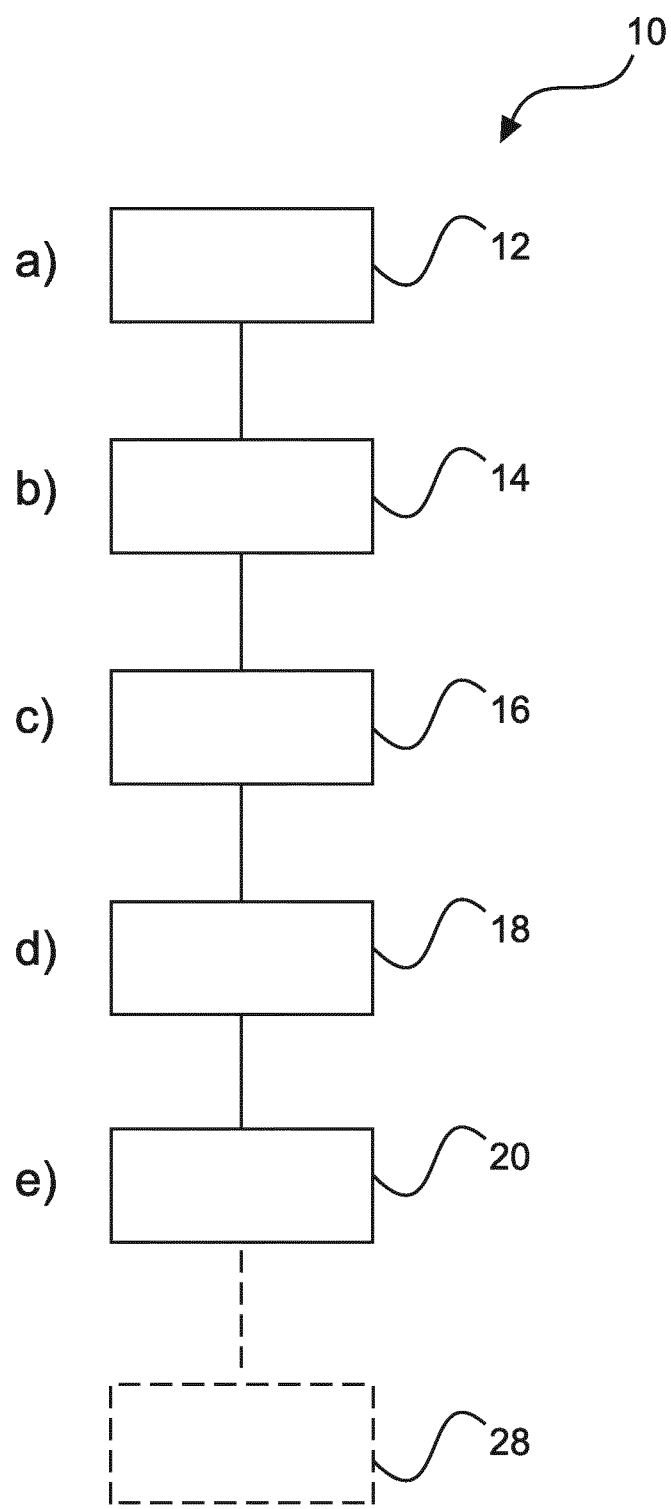
FIG. 1 shows an example of a method for determining optimal C-arm angulation for heart valve positioning.

FIG. 1 shows a method 10 for determining optimal C-arm angulation for heart valve positioning in its basic steps. The method comprises the following:

In a first providing step 12, also referred to as step a), a 2D image of an aortic root of a heart of a patient is provided. The 2D image comprises three cusps of the heart in a visible and distinct manner.

In an indication step 14, also referred to as step b), 2D positions of the three cusps in the 2D image are indicated.

In a second provision step 16, also referred to as step c), an analytical 3D model of the aortic cusp locations is provided.

In a first computing step 18, also referred to as step d), 3D positions of the three cusps are computed based on the 2D positions and the analytical 3D model.

In a second computing step 20, also referred to as step e), an optimal C-arm angulation is computed based on the computed 3D positions of the cusps. In the optimal C-arm angulation, the three cusps are aligned in a 2D image. The optimal C-arm angulation is further provided.

The 2D image is a 2D X-ray image. For example, the 2D image is provided as a 2D angiogram. The term "angiogram" relates to a visualization of the blood vessels of the heart region of the patient. In an example, the image is based on projective X-ray radiation. In an example, contrast agent is present during the acquisition of the 2D image.

In step a), a single 2D image, e.g. a single angiogram, is provided.

In the aligned state, the three cusps are arranged on a (virtual) common line.

The "analytical 3D model" relates to 3D information about the relative positioning of the three cusps. For example, the three cusps are approximately equidistant, with a standard distance in the order of the aortic radius.

The terms "visible and distinct" relate to showing the three cusps such that they can be identified, either manually or automatically.

According to an example, each cusp comprises a hinge point and, in the aligned state, the hinge points of the cusps are arranged on a common line.

Figure 2:
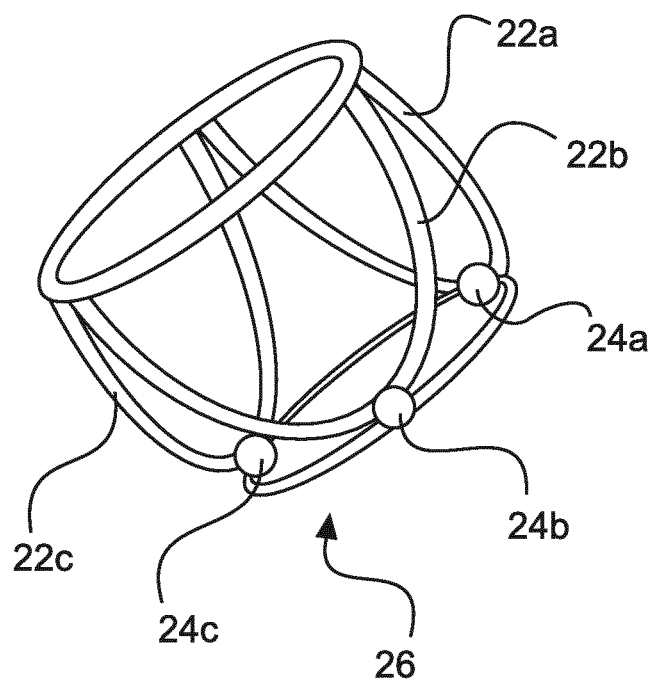
FIG. 2 shows a schematic illustration of three aortic cusps and their hinge points in a common plane.

For example, FIG. 2 shows a schematic setup of three aortic cusps 22a, 22b, and 22c. Further, hinge points 24a, 24b, and 24c are indicated. The hinge points 24a-c are arranged on a virtual common plane 26.

In an example, the indicating of the 2D positions of the three cusps in the 2D image (step b)) is based on determining the hinge points in the 2D image.

According to an example, not further shown, the three cusps are equidistant with a standard distance in the order of the aortic radius.

In an example, the current cusps are equidistant with a standard distance in the order of the current aortic radius, i.e. the aortic radius of the present patient.

In an example, not further shown, but provided as an option, the analytical 3D model comprises a spatial arrangement of the three cusps in a patient related manner.

The spatial arrangement of the cusps may be adapted to the (current) patient of interest. The analytical 3D model can also be referred to as a patient specific 3D model.

In an example, not further shown, the analytical 3D model is derived from 3D image data of the patient.

In a further example, the analytical 3D model is based on a patient specific model of the aortic cusps locations, wherein the patient specific model is derived from pre-operative 3D image data.

In another example, the analytical 3D model is based on a generic model, which is situation-specifically adapted to match with the current patient.

In an example, the pre-operative 3D image data relates to CT volume data. For example, the aorta has previously been segmented in 3D.

According to an example, not further shown in detail, the 2D image is a single live 2D X-ray image. As a further option, it is provided that the optimal C-arm angulation is provided for further acquisition of further live 2D X-ray images, as indicated in FIG. 1 as an option by a dotted frame 28 indicating the further acquisition.

For example, the live 2D X-ray images are provided as fluoroscopy images with contrast agent. In an example, the live 2D X-ray images are provided as angiograms.

In an example, the live 2D X-ray images are used for valve placement and deployment during TAVI procedures.

According to an example, the 2D image in step a) relates to a near-optimal C-arm angulation.

The term "near-optimal" relates to a deviation from the optimal C-arm angulation of maximum approximately +/−90°, for example a deviation of up to approximately +/−45°, such as 30° or less. In the perfect or optimal C-arm angulation, the three cusps are aligned in a 2D X-ray image taken in that optimal C-arm angulation.

Figure 3:
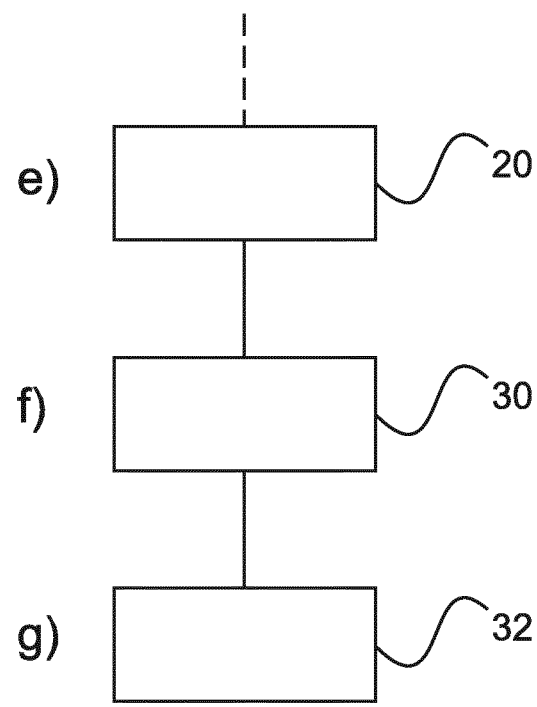
FIG. 3 shows a further example of a method for determining optimal C-arm angulation for heart valve positioning.

FIG. 3 shows a further example, according to which it is further provided a step f) of rotating 30 the C-arm to match the determined C-arm optimal angulation of step e). It is further provided a step g) of acquiring 32 2D image data.

The rotating of the C-arm may be performed by automatic position control (APC) or by manual interaction. Following step f), a valve positioning procedure may be provided, or also following step g) and the acquisition of further 2D image data in step g) can be used for monitoring the valve positioning procedure.

In another option, the indicating of the 2D positions of the three cusps of the heart in the 2D image is provided automatically by an automatic detection.

In another example, as a further option, the indicating of the 2D positions of the three cusps of the heart in the 2D image, e.g. the angiogram, is provided by manual user interaction.

Figure 4:
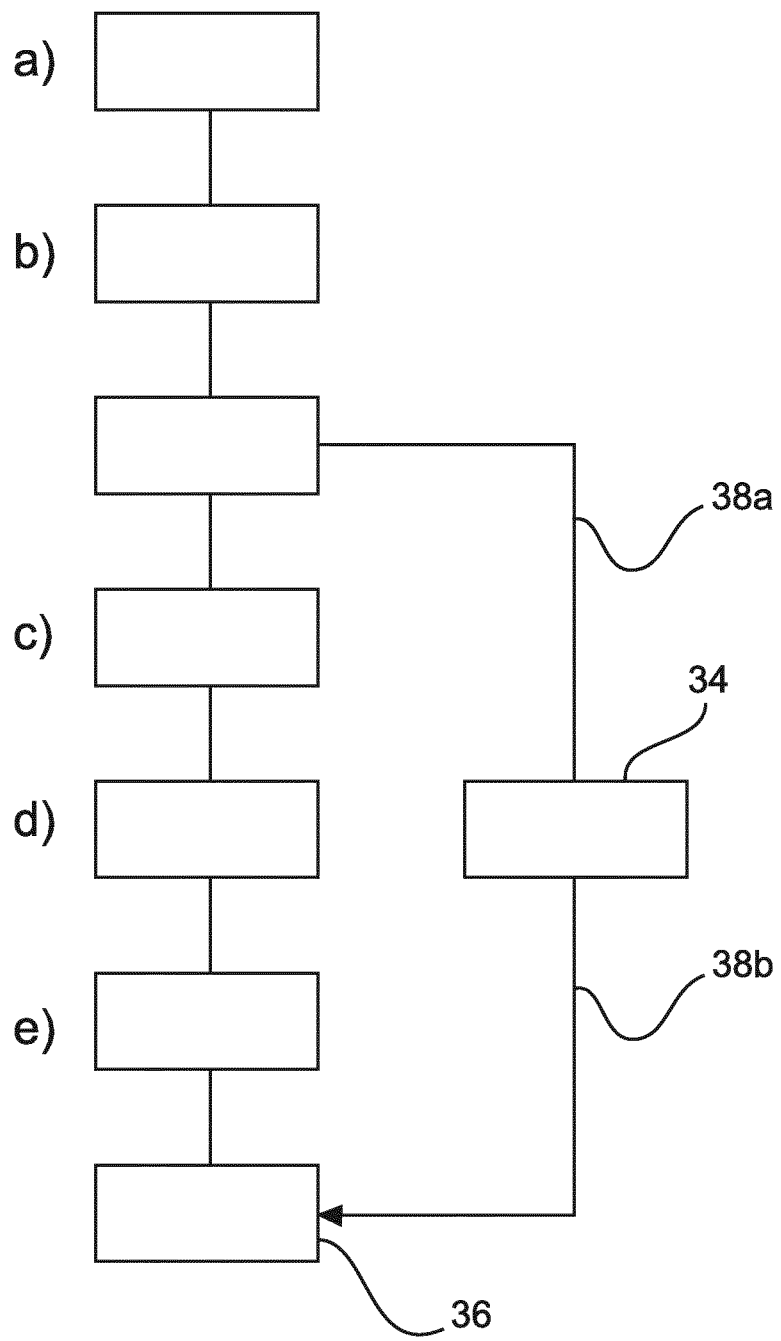
FIG. 4 shows another example of that method for determining optimal C-arm angulation for heart valve positioning.

FIG. 4 shows a further option, according to which, following step b), it is provided a step of checking 34 whether the three cusps are aligned. In case of alignment, the C-arm angulation used for the 2D image of step a) is provided as optimal C-arm angulation for further acquiring of 2D image data, which further acquiring is indicated with a further frame 36. Hence, step 34, as indicated by arrows 38a and 38b, so-to-speak bypasses steps c) to e) and thus further facilitates the procedure.

Figure 5:
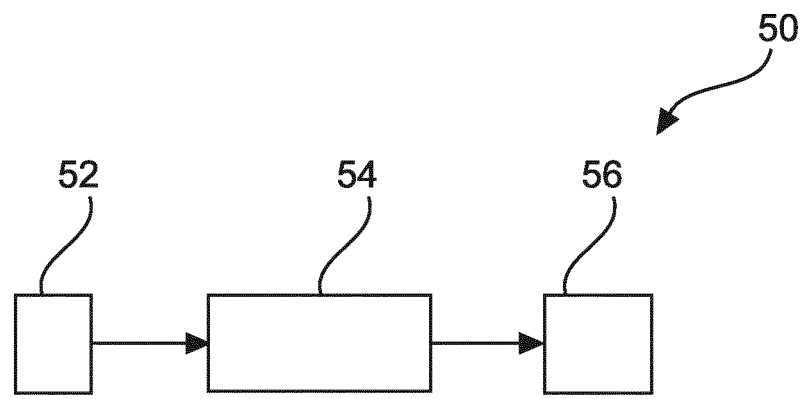
FIG. 5 shows a schematic setup of an example of an apparatus for determining optimal C-arm angulation for heart valve positioning.

FIG. 5 shows an example of an apparatus 50 for determining optimal C-arm angulation for heart valve positioning. The apparatus 50 comprises an input device 52, a processing device 54 and an output device 56. The input device 52 is configured to provide a 2D image of an aortic root of a heart of a patient. The 2D image comprises three cusps of the heart in a visible and distinct manner. The input device 52 is further configured to provide an analytical 3D model of the aortic cusp locations. The processing device 54 is configured to indicate 2D positions of the three cusps in the 2D image, and to compute 3D positions of the three cusps based on the 2D positions and the analytical 3D model. The processing device 54 is further configured to compute an optimal C-arm angulation based on the computed 3D positions of the cusps, wherein, in the optimal C-arm angulation, the three cusps are aligned in a 2D image. The output device 56 is configured to provide the optimal C-arm angulation.

In an example, the processing device is configured to provide the analytical 3D model of the aortic cusp locations. In a further example, the processing device comprises an interface device to indicate 2D positions of the three cusps in the 2D image by the user.

According to a further example, not further shown, the processing device is configured to provide the analytical 3D model comprising a spatial arrangement of the three cusps in a patient related manner.

Figure 6:
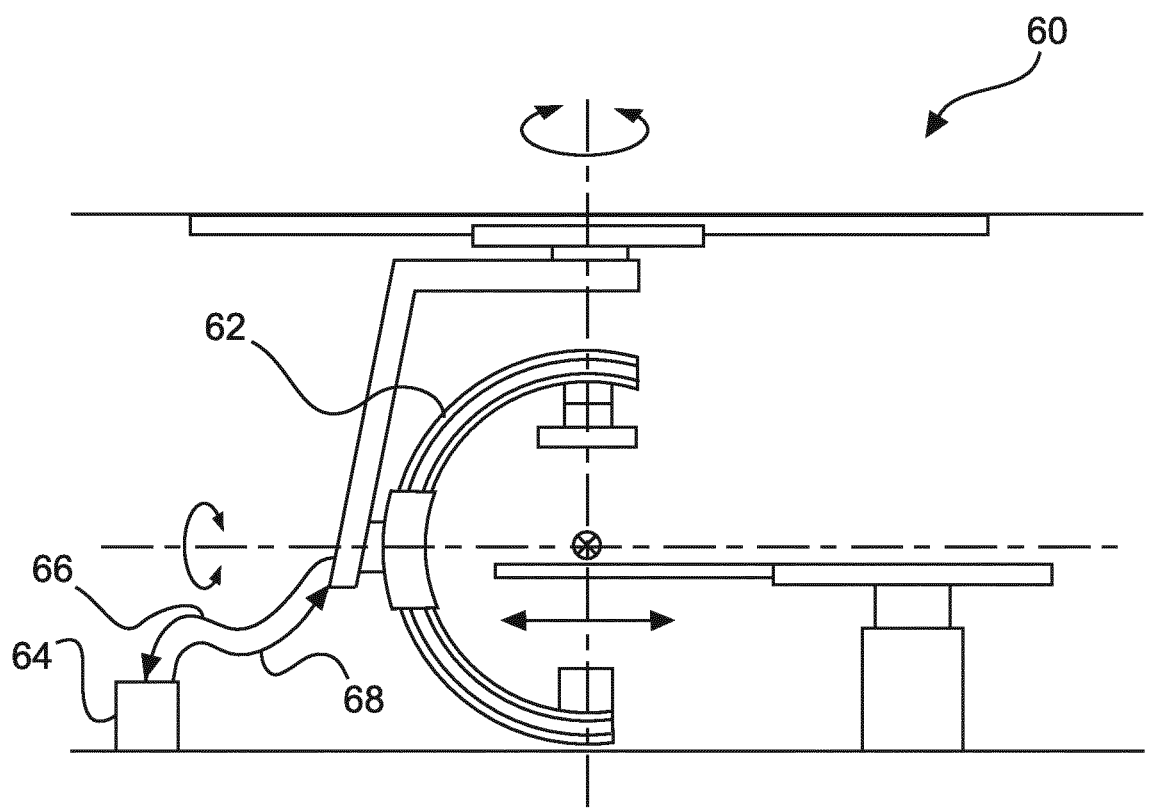
FIG. 6 shows a schematic setup of an example of a medical imaging system.

FIG. 6 shows a medical imaging system 60 comprising an X-ray imaging device 62 and an apparatus 64 for determining optimal C-arm angulation for heart valve positioning. The apparatus 64 is provided as an application according to the above-mentioned FIG. 5, i.e. the apparatus 50. The X-ray imaging device is configured to provide the 2D image as a live 2D X-ray image. The apparatus 64 is configured to provide the computed optimal C-arm angulation to the X-ray imaging device 62 for acquisition of further live 2D X-ray images. The provision of the 2D image from the imaging device to the apparatus is indicated with a first arrow 66. The provision of the computed optimal C-arm angulation to the X-ray imaging device is indicated with a second arrow 68. As mentioned above, the X-ray imaging device comprises a C-arm structure with an X-ray source and an X-ray detector attached to opposing ends of the C-arm.

The term "live" relates, for example, to providing images during an intervention, which images are acquired during that intervention, contrary to images that have been acquired before the intervention.

Figure 7:
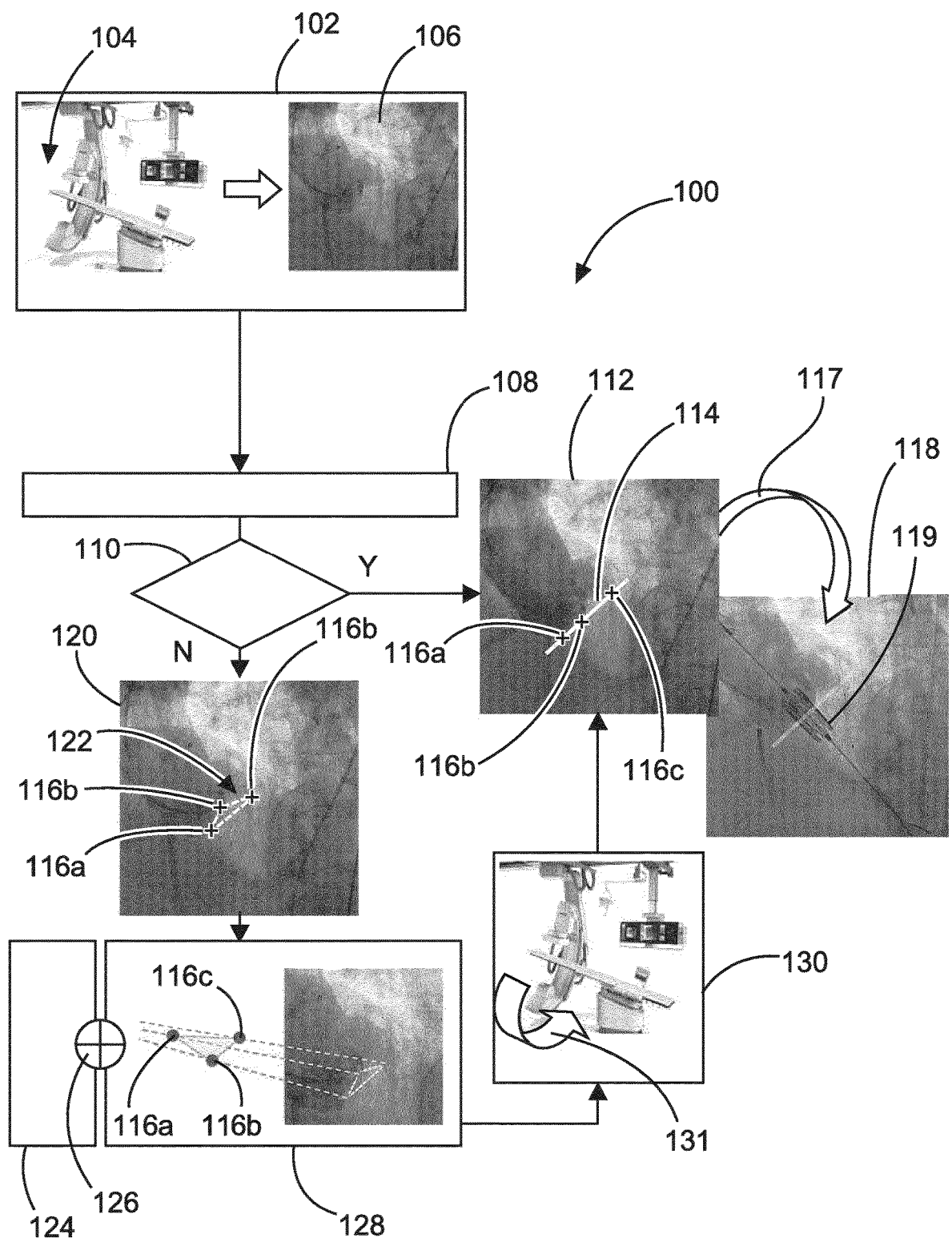
FIG. 7 shows an illustration of an example of a workflow for the method for determining optimal C-arm angulation.

FIG. 7 shows a further example of a detailed workflow 100. In a first step, indicated with a first frame 102, a near-optimal C-arm angulation 104 is used to acquire an angiogram 106 of the aortic root. In a further step 108, a frame of the angiogram is selected, in which the three cusps are visible. Further, the locations of the three cusps in this frame are selected.

Further, in a first decision step 110, it is checked whether the three cusps, i.e. the three landmarks in form of the hinge points, are aligned. If the result of this checking procedure is YES (indicated in FIG. 7 as "Y"), the alignment, indicated by image frame 112, showing a common line 114 upon which the three landmarks 116a, 116b, and 116c are arranged, this C-arm angulation is used (indicated by arrow 117) for a step 118 of valve positioning. The frame 118 shows a respective X-ray image taken during the valve positioning procedure, with an inserted device 119.

However, if the answer or result of the checking procedure is NO (indicated in FIG. 7 as "N"), the non-alignment is indicated with a further image frame 120, where the three landmarks 116a, 116b, and 116c are forming a triangular structure 122, different steps are provided. In a case of non-alignment, an analytical model of the aortic cusps locations is provided, as indicated with a further frame 124. Hence, it is assumed that the analytical model is known a priori, e.g. it can reasonably be assumed that the three cusps are equidistant, with the standard distance in the order of the aortic radius. This is then used to further determine the positions of the three landmarks in 3D, i.e. the three cusps' locations 116a, 116b, 116c, as indicated with computational step 126 and schematically illustrated in frame 128. It is then provided a further step of computing the optimal C-arm angulation to align the 3D landmarks in two-dimensional image runs. In a further step 130, the C-arm is moved accordingly (as indicated by arrow 131), for example via APC. The C-arm angulation is then used for a further image acquisition, resulting in the same or similar image, as the one described above with reference numeral 112, where the three cusps are aligned. This is then used for the valve positioning step 118.

In an example, the step of selecting the frame of the angiogram can be provided to be automatic or can be provided to be made manual (or automatic) by detecting a sufficiently injected frame.

The three cusps could also be automatically detected in a step of selecting the location of the three cusps as points of interests in the selected frame from the previous step.

In the step of the determining of the three landmarks positions in 3D, a patient specific model of the aortic cusp location can be used if a pre-operated 3D CT volume is available, and if the 3D aorta has been previously segmented.

Hence, the above-mentioned examples can be useful in the context of TAVI procedures, for example to enable accurate valve positioning and deployment, and thus to further improve the outcome of the intervention.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for determining a C-arm angulation for heart valve positioning, the apparatus comprising:
   an input device;
   a processing device; and
   an output device;
   wherein the input device is configured to provide a 2D image of an aortic root of a heart of a patient; wherein the 2D image comprises hinge points of three cusps of the heart in a visible and distinct manner; and to provide an analytical 3D model of locations of the three cusps;
   wherein the processing device is configured to indicate 2D positions of the hinge points of the three cusps in the 2D image; to compute 3D positions of the hinge points of the three cusps based on the 2D positions and the analytical 3D model; and to compute the C-arm angulation based on the computed 3D positions so that the hinge points of the three cusps are aligned in a further 2D image acquired using said C-arm angulation; and
wherein the output device is configured to provide the C-arm angulation.

2. The apparatus according to claim 1, wherein the processing device is configured to provide the analytical 3D model comprising a spatial arrangement of the three cusps in a patient related manner.

3. A medical imaging system, comprising:
an X-ray imaging device; and
an apparatus for determining a C-arm angulation for heart valve positioning according to claim 1;
wherein the X-ray imaging device is configured to provide the 2D image as a live 2D X-ray image; and
wherein the apparatus is configured to provide the optimal C-arm in angulation to the X-ray imaging device for acquisition of the further 2D image as a live 2D X-ray image.

4. The apparatus according to claim 1, wherein the C-arm angulation is computed based on the computed 3D positions of the three cusps so that the aligned hinge points of the three cusps are equidistant with a standard distance in an order of an aortic radius.

5. The apparatus according to claim 1, wherein the analytical 3D model is based on a patient specific model of locations of the three cusps; and
wherein the patient specific model is derived from pre-operative 3D image data.

6. The apparatus according to claim 1, wherein the 2D image is a single live 2D X-ray image; and
wherein the optimal C-arm angulation is provided for further acquisition of further live 2D X-ray images.

7. The apparatus according to claim 1, wherein the provided 2D image of the aortic root relates to a near-optimal C-arm angulation.

8. The apparatus according to claim 1, wherein the indicating of the 2D positions of the hinge points of the three cusps of the heart in the 2D image is provided automatically by an automatic detection.

9. A method for determining optimal C-arm angulation for heart valve positioning, the method comprising:
providing a 2D image of an aortic root of a heart of a patient; wherein the 2D image comprises hinge points of three cusps of the heart in a visible and distinct manner;
indicating 2D positions of the hinge points of the three cusps in the 2D image;
providing an analytical 3D model of the hinge points of the three cusps;
computing 3D positions of the hinge points of the three cusps based on the 2D positions and the analytical 3D model; and
computing an C-arm angulation based on the computed 3D positions of the three cusps such that, in a further 2D image acquired using the C-arm angulation, the hinge points of the three cusps are aligned; and
providing the optimal C-arm angulation.

10. The method according to claim 9, wherein the aligned hinge points of the three cusps are equidistant with a standard distance in an order of an aortic radius.

11. The method according to claim 9, wherein the analytical 3D model comprises a spatial arrangement of the hinge points of the three cusps in a patient related manner.

12. The method according to claim 9, wherein the analytical 3D model is based on a patient specific model of locations of the three cusps; and
wherein the patient specific model is derived from pre-operative 3D image data.

13. The method according to claim 9, wherein the 2D image is a single live 2D X-ray image; and
wherein the optimal C-arm angulation is provided for further acquisition of further live 2D X-ray images.

14. The method according to claim 9, wherein the provided 2D image relates to a near-optimal C-arm angulation.

15. The method according to claim 9, further comprising:
rotating a C-arm to match the determined C-arm optimal angulation; and
acquiring 2D image data.

16. The method according to claim 15, wherein the indicating of the 2D positions of the hinge points of the three cusps of the heart in the 2D image is provided automatically by an automatic detection.

17. The method according to claim 16, further comprising:
checking whether the hinge points of the three cusps are aligned after indicating the 2D positions of the three cusps in the 2D image; wherein in case of alignment, the C-arm angulation used for the 2D image is provided as the optimal C-arm angulation for further acquiring of 2D image data.

18. A non-transitory computer readable medium having stored thereon software instructions that, when executed by a processor, cause the processor to determine optimal C-arm angulation for heart valve positioning, by executing steps comprising:
acquiring a 2D image of an aortic root of a heart of a patient; wherein the 2D image comprises hinge points of three cusps of the heart in a visible and distinct manner;
indicating 2D positions of the hinge points of the three cusps in the 2D image;
retrieving an analytical 3D model of the three cusps;
determining 3D positions of the hinge points of the three cusps based on the 2D positions and the analytical 3D model;
determining an C-arm angulation based on the determined 3D positions of the three cusps, such that the hinge points of the three cusps are aligned in a further 2D image acquired using the C-arm angulation; and
providing the optimal C-arm angulation.

* * * * *